US009795709B2

(12) United States Patent
Kuntz et al.

(10) Patent No.: US 9,795,709 B2
(45) **Date of Patent: *Oct. 24, 2017**

(54) CERAMIC COMPOSITE MATERIAL CONSISTING OF ALUMINIUM OXIDE AND ZIRCONIUM OXIDE AS MAIN CONSTITUTENTS

(75) Inventors: Meinhard Kuntz, Esslingen (DE); Michael Kuntz, Homburg (DE); Lukas Gottwik, Heiningen (DE); Kristina Schilcher, Esslingen (DE); Andreas Morhardt, Esslingen (DE); Kilian Friederich, Plochingen (DE); Norbet Schneider, Schorndorf (DE)

(73) Assignee: CeramTec GmbH, Plochingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/515,405

(22) PCT Filed: Dec. 16, 2010

(86) PCT No.: PCT/EP2010/069991

§ 371 (c)(1), (2), (4) Date: Jun. 21, 2012

(87) PCT Pub. No.: WO2011/083022

PCT Pub. Date: Jul. 14, 2011

(65) Prior Publication Data

US 2012/0252655 A1 Oct. 4, 2012

(30) Foreign Application Priority Data

Dec. 16, 2009 (DE) ..................... 10 2009 054 796.7
Dec. 16, 2009 (DE) ..................... 10 2009 054 797

(51) Int. Cl.

| | |
|---|---|
| ***C04B 35/10*** | (2006.01) |
| ***A61L 27/04*** | (2006.01) |
| ***A61L 31/02*** | (2006.01) |
| ***C04B 35/119*** | (2006.01) |
| ***C04B 35/645*** | (2006.01) |

(52) U.S. Cl.

CPC ........... *A61L 27/047* (2013.01); *A61L 31/026* (2013.01); *C04B 35/119* (2013.01); *C04B 35/6455* (2013.01); *C04B 2235/3206* (2013.01); *C04B 2235/3208* (2013.01); *C04B 2235/3225* (2013.01); *C04B 2235/3229* (2013.01); *C04B 2235/3246* (2013.01); *C04B 2235/5445* (2013.01); *C04B 2235/662* (2013.01); *C04B 2235/72* (2013.01); *C04B 2235/765* (2013.01); *C04B 2235/785* (2013.01)

(58) Field of Classification Search

CPC ..... A61L 27/105; A61L 31/026; C04B 35/119
USPC ......................................................... 501/105
See application file for complete search history.

(56) References Cited

U.S. PATENT DOCUMENTS

| | | | | |
|---|---|---|---|---|
| 4,419,311 | A * | 12/1983 | Claussen et al. | 264/681 |
| 4,771,022 | A * | 9/1988 | Block et al. | 501/103 |
| 4,810,680 | A * | 3/1989 | Bickford et al. | 501/103 |
| 4,820,667 | A * | 4/1989 | Tsunekawa et al. | 501/104 |
| 5,002,911 | A * | 3/1991 | Matsumoto et al. | 501/105 |
| 5,032,555 | A | 7/1991 | Yamanis et al. | |
| 5,082,809 | A * | 1/1992 | Hayashi | 501/105 |
| 5,830,816 | A * | 11/1998 | Burger et al. | 501/105 |
| 6,452,957 | B1 * | 9/2002 | Burger et al. | 373/137 |
| 7,148,167 | B2 * | 12/2006 | Shikata et al. | 501/105 |
| 7,399,722 | B2 * | 7/2008 | Shikata et al. | 501/105 |
| 7,820,577 | B2 * | 10/2010 | Shikata et al. | 501/105 |
| 2002/0010070 | A1 * | 1/2002 | Cales et al. | 501/105 |
| 2005/0049137 | A1 * | 3/2005 | Shikata et al. | 501/105 |
| 2006/0063661 | A1 * | 3/2006 | Cohen | 501/105 |
| 2010/0120605 | A1 | 5/2010 | Kuntz et al. | |
| 2010/0137972 | A1 | 6/2010 | Kuntz et al. | |
| 2010/0152018 | A1 * | 6/2010 | Kuntz et al. | 501/104 |

FOREIGN PATENT DOCUMENTS

| | | | |
|---|---|---|---|
| EP | 2 168 936 | A1 | 3/2010 |
| JP | 04275977 | * | 10/1992 |
| JP | 2000344569 | * | 12/2000 |
| WO | WO 01/80783 | A2 | 11/2001 |
| WO | WO 2008/132157 | A2 | 11/2008 |
| WO | WO 2008/132158 | A1 | 11/2008 |
| WO | WO 2008/132159 | A1 | 11/2008 |

OTHER PUBLICATIONS

Machine translation of JP 2000344569, Dec. 2000.*

Becher, Paul F. "Transient Thermal Stress Behavior in $ZrO_2$-Toughened $Al_2O_3$", *J. Am, Ceram. Soc.* 64, No. 1 (1981), pp. 37-39.

De Aza, et al. "Slow-Crack—Growth Behavior of Zirconia-Toughened Alumina Ceramics Processed by Different Methods", *J. Am, Ceram. Soc.* 86 [1] (2003), pp. 115-120.

In Kollenberg, W. Technische Keraminik Grundlagen, Werkstoffe, Verfahrenstechnik; 2 Auflage; "Ceramic Materials", Vulkam Verlag, Essen, 2009; XP002629667; pp. 231-250 (with English translation).

(Continued)

*Primary Examiner* — Karl Group

(74) *Attorney, Agent, or Firm* — Norton Rose Fulbright US LLP

(57) ABSTRACT

A composite material having a first phase includes an aluminum oxide proportion of at least 65% by volume and a second phase comprising a zirconium proportion of 10 to 35% by volume. The zirconium is present as zirconium oxide. The aluminum oxide is a ceramic matrix and the zirconium oxide is dispersed therein. From 90 to 99% of the zirconium oxide is present in the tetragonal phase. A chemical stabilizer for stabilizing the tetragonal phase of the zirconium oxide is also present. The total content of chemical stabilizer is <0.2 mol % relative to the zirconium oxide content.

9 Claims, No Drawings

(56) References Cited

OTHER PUBLICATIONS

Rahaman, et al. "Ceramics for Prosthetic Hip and Knee Joint Replacement", *J. Am Ceram. Soc.* 90 [7], (2007), XP-0002630077, pp. 1965-1988.
Hannink, et al. "Transformation Toughening in Zirconia-Containing Ceramics", *J. Am, Ceram. Soc.* 83 [3], (2000), pp. 461-487.

* cited by examiner

CERAMIC COMPOSITE MATERIAL CONSISTING OF ALUMINIUM OXIDE AND ZIRCONIUM OXIDE AS MAIN CONSTITUTENTS

This application is a §371 of PCT/EP2010/069991, filed on Dec. 16, 2010, and claims priority from German Patent Application Nos. 102009054797.5 and 102009054796.7, each filed on Dec. 16, 2009.

FIELD OF THE INVENTION

The present invention relates to a composite consisting of aluminum oxide as a ceramic matrix and zirconium oxide dispersed therein, a method for the production thereof, and the use of the same.

BACKGROUND OF THE INVENTION

The molecular structures of metallic alloys and ceramic materials differ substantially from each other. In the metallic bond, the electrons orbit the atomic nuclei disorderly and with comparatively low bonding force. Ions, for example in the body environment, separate constantly from this "loose" structure; a variety of chemical reactions are possible.

In ceramic molecules, the electrons in the ceramic bond follow precisely predefined paths, the so-called directed electron orbitals. Their bonding force is very high; the molecules are extremely stable. Therefore, no formation of ions takes place and chemical reactions are virtually impossible.

OBJECT AND SUMMARY OF THE INVENTION

The extremely stable ceramic bond almost excludes plastic deformation of the material. This effects, on the one hand, the desired extremely high hardness, but, on the other, it results in relatively high brittleness, However, with the correct material design, it is possible to achieve high hardness and high ductility at the same time.

Material science distinguishes between fracture strength and fracture toughness. Fracture strength is the maximum mechanical stress a material resists without breaking. Fracture toughness, or crack initiation toughness, describes the resistance of a material against the onset of crack propagation. Ceramic materials which have very high fracture strength are today already in use in medical technology. Some of these materials have in addition extremely high fracture toughness. Such materials have a much better resistance against the onset of cracks than other ceramics and can retard the growth of the crack.

This property is based on two reinforcement mechanisms. The first reinforcement mechanism is owed to the embedded tetragonal, zirconium oxide nanoparticles. These particles are individually distributed in the aluminum oxide matrix. They generate local pressure peaks in the region of the cracks and counteract crack propagation in this manner.

DETAILED DESCRICTION

The second reinforcement mechanism is achieved through platelet-shaped crystals which likewise form sporadically in the oxide mixture. These "platelets" deflect potential cracks, disperse crack energy and thus dissipate energy. Both functions with such materials also allow constructing component geometries which were not achievable in the past with ceramics.

The object underlying the present invention was to further improve the properties of the known ceramic materials.

The present invention relates to a ceramic composite material consisting of the main constituents, aluminum oxide and zirconium oxide, as well as one or a plurality of inorganic aggregates by means of which the properties of the composite material can be influenced. Here, aluminum oxide forms the main component with a volume content of >65%, preferably 85 to 90%; zirconium oxide forms the secondary component, with a volume content between 10 and 35%, Furthermore, aluminum oxide as well as zirconium oxide can also contain soluble constituents. As soluble constituents, one or a plurality of the following elements can be present: Cr, Fe, Mg, Ti, Y, Ce, Ca, lanthanides and/or V. In the initial state, zirconium oxide is present in a. large proportion, preferably 80 to 99%, particularly preferred 90 to 99% based on the total zirconium content, in the tetragonal phase. The known phase transformation of zirconium oxide from tetragonal to monoclinic is utilized in the composite material according to the invention as a reinforcement mechanism, in order to favorably influence fracture toughness and strength.

Stabilizing the tetragonal phase of zirconium oxide in the composite material according to the invention surprisingly takes place for the most part not chemically but mechanically. Thus, the content of inorganic chemical stabilizers relative to zirconium oxide is limited to values which are considerably lower than the contents normally used in the prior art. $Y_2O_3$ is the chemical stabilizer which is usually and preferably used in the prior art. Further known stabilizers are $CeO_2$ CaO and MgO, Examples of known formulations for ceramic composite materials are:

| Designation | Mol % $Y_2O_3$ based on $ZrO_2$ |
|---|---|
| Y-TZP [(1)] | 2.8 or 3.2 |
| ZTA [(2)] | 1.3 |

[(1)] Yttrium toughened Zirconia
[(2)] Zirconia toughened Alumina.

In the composite material according to the invention, a stabilizer content is used which is considerably lower than the contents used in the prior art. This is possible according to the invention in that in the composite material according to the invention, the zirconium oxide is embedded into the aluminum, oxide matrix in such a manner that by embedding into the matrix, said zirconium oxide is stabilized in the metastable tetragonal phase (mechanical stabilization).

A requirement for mechanical stabilization is an aluminum oxide proportion of at least 65% by volume, preferably 65 to 90% by volume, with a zirconium oxide proportion of 10 to 35% by volume. Of particular importance for the surprisingly achievable mechanical stabilization according to the invention is the grain size of the zirconium oxide particles in the composite material according to the invention. The grain size of the zirconium particles should on average not exceed 0.5 μm (measured according to the linear intercept method). Preferred for the composite material mechanically stabilized according to the invention are zirconium particles with a grain size on average from 0.1 μm to 0.2 μm, 0.2 μm to 0.3 μm, 0.3 μm to 0.4 μm, or 0.4 μm to 0.5 μm, preferred from 0.1 to 0.3 μm, particularly preferred from 0.15 μm to 0.25 μm.

The proportion of chemical stabilizers in the composite material according to the invention (proportion in each case relative to the zirconium content) is for $Y_2O_3 \leq 1.5$ mol %, preferred ≤1.3 mol %, for $CeO_2 \leq 3$ mol %, for MgO≤3 mol % and for CaO≤3 mol %, Particularly preferred is a total stabilizer content of less than 0.2 mol %. Particularly preferred according to the invention is a mechanically stabilized composite material that contains no chemical stabilizer.

It is known that materials which are stabilized by using chemical stabilizers, in particular materials stabilized by $Y_2O_3$, are prone to hydrothermal aging. In these materials, spontaneous phase transformation occurs in presence of water molecules at elevated temperatures, for example, already at body temperature. The reason for this sensitivity to water at elevated temperatures is the formation of oxygen vacancies in the zirconium oxide lattice, which vacancies then can be filled with hydroxide ions. This phenomenon is called "hydrothermal aging".

The composite material according to the invention is considerably less prone to hydrothermal aging than materials which are stabilized through the use of chemical stabilizers, in particular through the use of $Y_2O_3$.

Through the reduced content of chemical stabilizers, the zirconium oxide lattice in the composite material according to the invent ion contains proportionally less oxygen vacancies. Thus, the composite material according to the invention reacts less sensitive to the presence of water at elevated temperatures as is the case for materials known from the prior art: the composite material according to the invention is considerably less prone to hydrothermal aging.

The production of the composite material according to the invention is carried out by means of conventional ceramics technology known per se. The essential process steps are, for example:

a) Preparing the powder mixture according to specified composition in water; if necessary, use of liguefiers to prevent sedimentation.
b) Homogenizing in a dissolver (high-speed stirrer).
c) Milling in an agitator ball mill, thereby increasing the specific surface area of the powder mixture (=comminution).
d) If necessary, adding organic binders.
e) Spray drying, thereby creating free-flowing granulate with defined properties, Wetting the granulate with water, g) Axial or isostatic pressing.
h) Green machining, thereby substantially mapping the final contour under consideration of the sinter shrinkage.
i) Prefiring, thereby reduction to approx. 98% of the theoretical density. The still remaining residual pores are closed toward the outside.
j) Hot isostatic pressing at high temperature and high gas pressure, practically resulting in full final density.
k) So-called clean burn; as a result, the imbalance generated during hot isostatic pressing of the oxygen ions in the ceramic is balanced.
l) Hard machining by grinding and polishing.
m) Annealing.

The composite material according to the invention can be used, for example, for producing sintered bodies, for producing components having the ability of absorbing energy under dynamic load in medical technology, for producing orthoses and endoprostheses, for example for hip joint and knee joint implants, drills, for example for medical applications, machine tool components which are triboiogically, chemically and/or thermally stressed.

The present invention thus relates to a composite material from aluminum oxide as a ceramic matrix, zirconium oxide dispersed therein, and optionally further aggregates/phases, wherein the composite material contains as a first phase an aluminum oxide proportion of at least 65% by volume and as a second phase a zirconium proportion of 10 to 35% by volume and, optionally, one or a plurality of inorganic aggregates, and wherein, based on the total zirconium oxide content, the largest portion of the zirconium oxide, preferably 80 to 99%, particularly preferred 90 to 99%, is present in the tetragonal phase, and wherein stabilizing the tetragonal phase takes place predominantly not chemically, but mechanically.

Particularly preferred is a composite material according to the invention in which the zirconium particles have a grain size on average of 0.1to 0.5 μm, preferably on average of 0.15 to 0.25 μm;
the content of chemical stabilizers relative to the zirconium oxide is limited to values which are significantly lower than the ones for the respective chemical stabilizers used in the prior art;
the content of chemical stabilizers in the composite material according to the invention (proportion in each case relative to the zirconium content) is for $Y_2O_3 \leq 1.5$ mol %, preferred ≤1.3 mol %, for $CeO_2 \leq 3$ mol %, for MgO≤3 mol % and for CaO≤3 mol %;
the total content of chemical stabilizers is <0.2 mol %;
the composite material contains no chemical stabilizer;
the aluminum oxide and/or the zirconium oxide contains soluble constituents;
as soluble constituents in the aluminum oxide and/or in the zirconium oxide, one or a plurality of the following elements are present; Cr, Fe, Mg, Ti, Y, Ce, Ca, lanthanides and/or V.

Furthermore, the present invention relates to the use of the composite material according to the invention for producing sintered bodies;
for producing components having the ability of absorbing energy under dynamic load;
in medical technology;
for producing artificial prostheses in the field of medical technology, for example for producing orthoses and endoprostheses;
for producing hip joint and knee joint implants.

It is claimed:

1. A composite material comprising:

a first phase, said first phase comprising at least 65% by volume aluminum oxide;
a second phase, said second phase comprising 10 to 35% by volume zirconium, wherein said zirconium is present as zirconium oxide, and wherein 90 to 99% of said zirconium oxide is present in a tetragonal phase; and
a chemical stabilizer for stabilizing said tetragonal phase of said zirconium oxide;
wherein said chemical stabilizer for stabilizing said tetragonal phase of said zirconium oxide is present in a total amount of <0.2 mol % relative to said zirconium oxide content;
wherein said aluminum oxide is present as a ceramic matrix; and
wherein said zirconium oxide is dispersed in said ceramic matrix.

2. The composite material according to claim 1, wherein said zirconium oxide is present as particles having a grain size on average of 0.1 to 0.5 μm.

3. A sintered body comprising a sintered composite according to claim 1.

4. A component comprising a sintered composite according to claim 1, wherein said component absorbs energy under dynamic load.

5. The component of claim 4, wherein said component is a medical component.

6. The component of claim 5, wherein said component is a prosthetic.

7. The component of claim 6, wherein said component is a hip joint implant or a knee joint implant.

8. The composite material according to claim 1, wherein said zirconium oxide is present as particles having a grain size on average of 0.15 to 0.25 μm.

9. The composite material according to claim 1, wherein said chemical stabilizer comprises at least one member selected from the group consisting of $Y_2O_3$, $CeO_2$, CaO and MgO.

* * * * *